United States Patent [19]

Berlin

[11] Patent Number: 5,453,008
[45] Date of Patent: Sep. 26, 1995

[54] CONTRA-ANGLE HEAD FOR ENDODONTIC INSTRUMENT

[75] Inventor: Pierre Berlin, La Chaux-De-Fonds, Switzerland

[73] Assignee: Instruments Dentaires S.A., La Chaux-De-Fonds, Switzerland

[21] Appl. No.: 218,312

[22] Filed: Mar. 24, 1994

[30] Foreign Application Priority Data

Apr. 13, 1993 [CH] Switzerland ............... 1105/93

[51] Int. Cl.⁶ .................. A61C 1/07; A61C 3/03; A61C 3/08
[52] U.S. Cl. ............... 433/122; 433/118
[58] Field of Search .............. 433/118, 119, 433/122, 123

[56] References Cited

U.S. PATENT DOCUMENTS

| | | | |
|---|---|---|---|
| 610,987 | 9/1898 | Hendrickson et al. | 433/123 |
| 3,073,031 | 1/1963 | Brenman et al. | 433/122 |
| 4,175,324 | 11/1979 | Arai | 433/122 |
| 4,460,341 | 7/1984 | Nakanishi | 433/122 |
| 4,544,356 | 10/1985 | Gardella et al. | 433/122 |
| 4,834,653 | 5/1989 | Edwardson | 433/118 |

FOREIGN PATENT DOCUMENTS

| | | |
|---|---|---|
| 0064871 | 11/1982 | European Pat. Off. |
| 0161196 | 11/1985 | European Pat. Off. |
| 295550 | 8/1928 | United Kingdom. |
| 9118555 | 12/1991 | WIPO. |

OTHER PUBLICATIONS

International Search Report of Counterpart Swiss Application 1105/93.

Primary Examiner—Nicholas D. Lucchesi

[57] ABSTRACT

A dental handpiece head comprises a tool holder (17) driven by an eccentric crankpin (10) engaged in a vertical groove (18) of the tool holder. The axial displacement of the tool holder is limited by a finger (13) engaged in a transverse cutting (12) of the tool holder, the walls of which cutting define two axial limit stops. The relative position of these limit stops and of the groove (18) is such that when the tool holder is pushed back by the reaction to the penetration of the tool into the dental canal, the tool holder is driven only in alternating rotation, whereas it is driven in a combined rotational and translational movement when a traction force is exerted on the tool.

This construction has the effect of suppressing the percussions of the tool in the tooth.

2 Claims, 3 Drawing Sheets

CONTRA-ANGLE HEAD FOR ENDODONTIC INSTRUMENT

FIELD OF THE INVENTION

The present invention relates to a contra-angle head for an endodontic instrument, having a bore in which is mounted a cylindrical tool holder having a groove parallel to the axis of the bore and in which is engaged a crankpin supported in an eccentric manner by a drive shaft driven in a rotational movement in such a way as to drive the tool holder in its bore both in an alternating rotational movement and in an alternating translational movement.

PRIOR ART

Such a contra-angle head is known in particular from the patent documents EP 0,161,196 and EP 0,230,846.

Instruments are also known in which the tool holder is driven only in an alternating rotational movement. Such an instrument is described, for example, in the patent document EP 0,064,871.

A combined rotational and translational movement has the effect of increasing substantially the efficacy of the tool compared to a rotational movement. However, when the operator causes the tool to penetrate into a dental canal, the alternating axial movement generates a series of very troublesome percussions to the detriment of the tactile sensitivity necessary during this type of operation. These percussions can be compared, relatively speaking, to those produced by a pneumatic drill. These vibrations are also unpleasant for the patient.

SUMMARY OF THE INVENTION

The aim of the present invention is to obviate this disadvantage, that is to say to suppress these percussions.

To this end, the contra-angle head according to the invention is characterized by the fact that the length of said groove is greater than the outer diameter of the circle described by the crankpin, and the cylindrical tool holder is additionally mounted in the bore of the head with an axial play limited by two limit stops, the position of these limit stops relative to the ends of the groove, viewed in a direction parallel to the axis of the bore, being such that when the tool holder is pushed back against one of the limit stops, the groove extends over at least the whole axial travel of the crankpin, such that the tool holder is not driven in translation during the rotation of the crankpin, and when the tool holder is in abutment against the other limit stop, the axial offset between the groove and the axial travel of the crankpin ensures that the tool holder is driven in translation.

When the operator carries out penetrative work, that is to say with an axial pressure on the head, the reaction due to the resistance to the advance has the exact effect of pushing the tool holder back such that the alternating axial movement is suppressed and, with it, the percussions and the vibrations transmitted to the contra-angle. The operator thus retains all the tactile sensitivity necessary for a precise and controlled penetration of the tool into the dental canal.

On the other hand, as soon as the operator begins a maneuver to withdraw the tool, the frictional forces on the tool have the effect of exerting a traction on the tool holder such that the latter comes into abutment against the opposite limit stop, and the tool holder is driven in a combined rotational and translational movement.

This combined movement ensures an axial filing of the dental canal and confers upon the tool a considerable efficacy in the operation for widening the coronal third of the canal, as well as an excellent removal of the dentinal debris.

The suppression of the axial movement during the phase of penetration of the tool additionally makes it possible to increase the amplitude of the rotational movement and, consequently, the efficacy of the tool.

The attached drawing represents, by way of example, an embodiment of the invention and alternatives thereof.

DESCRIPTION OF THE PREFERRED EMBODIMENT

Figure 1:
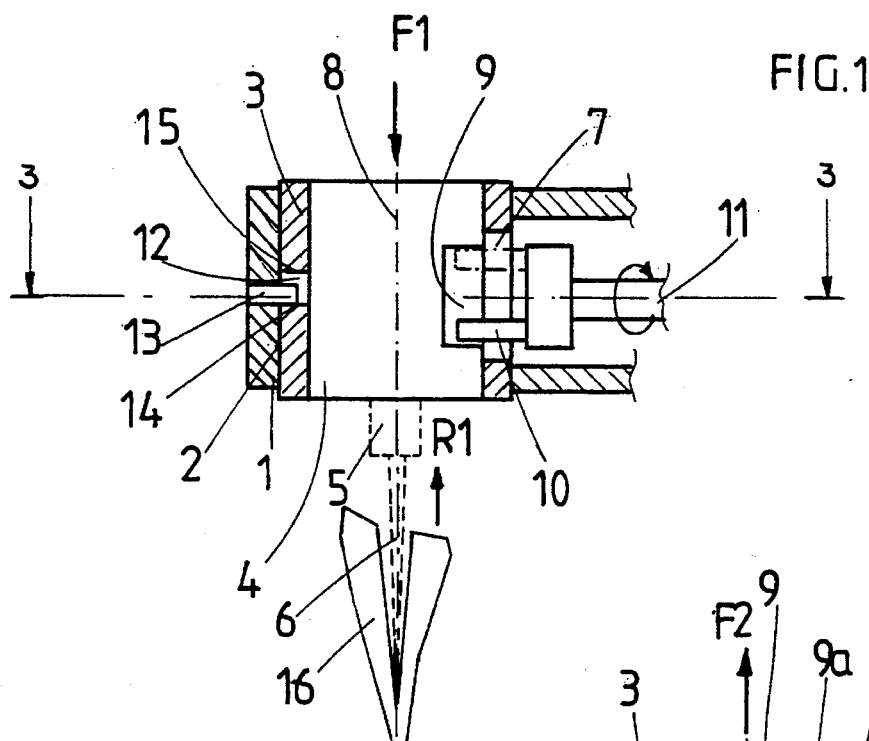
FIG. 1 is an axial cutaway view, along I—I in FIG. 3, of a contra-angle head, in a first embodiment, showing the tool holder in abutment against one of its limit stops.
Figure 2:
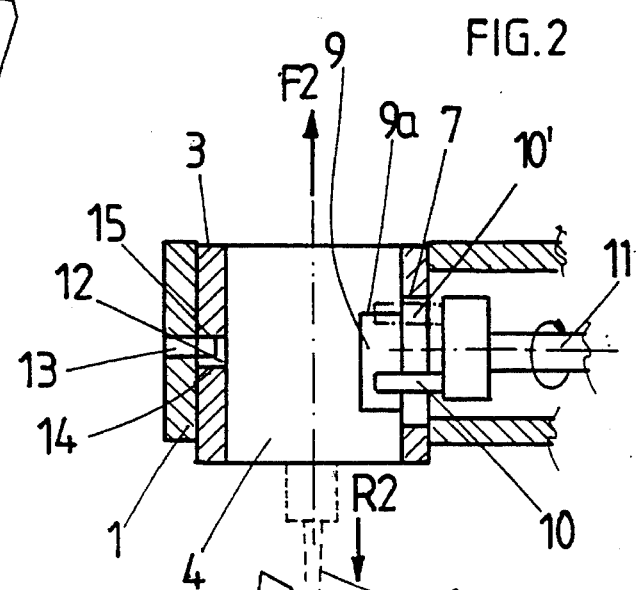
FIG. 2 is a view similar to FIG. 1, showing the tool holder in abutment against the other limit stop.
Figure 3:
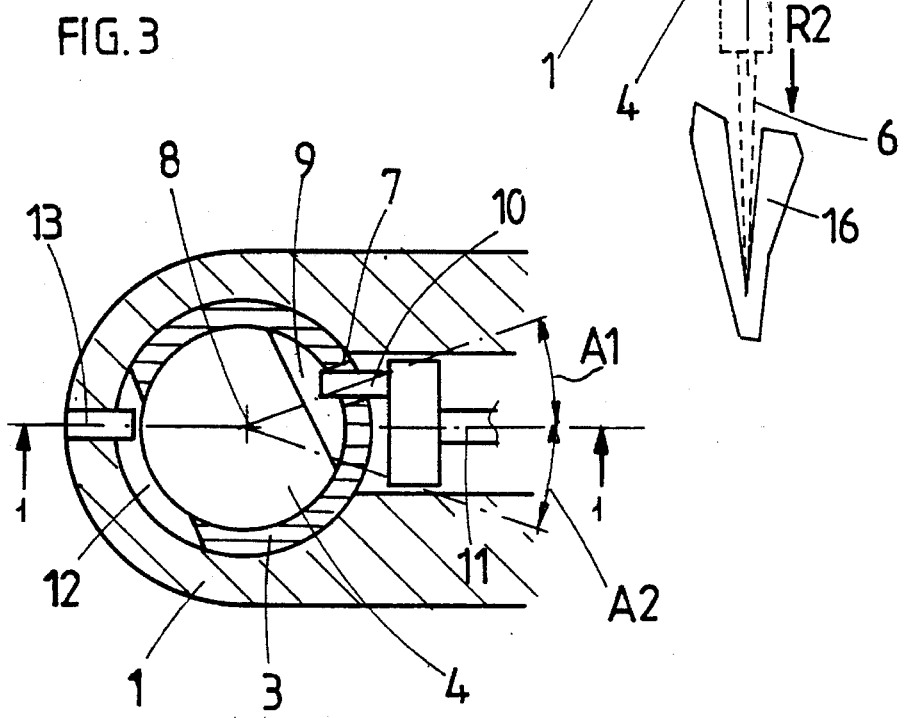
FIG. 3 is a cutaway view along III—III in FIG. 1.

FIGS. 1 to 3 show a contra-angle head 1 having a cylindrical bore 2 in which is mounted a cylindrical sheath 3 in which is fixed a sleeve 4. The sheath 3 and the sleeve 4 constitute a tool holder in which is housed a clamping device for a mandrel 5 represented in broken lines, in which mandrel there is fixed a tool 6, also represented in broken lines. The sheath 3 has, on the one hand, an oblong slot 7 parallel to the axis 8 of the bore and, level with this slot 7 the sleeve 4 has a transverse cutting 9. The superimposition of the slot 7 and of the cutting 9 defines a groove parallel to the axis 8 of a length equal to the height of the cutting 9 and of a width equal to the width of the slot 7. Engaged in this groove is a crankpin 10 which is mounted eccentrically on the end of a drive shaft 11, which is itself driven by any known means. The height of the cutting 9, that is to say the length of the groove, is greater than the diameter of the outer circle circumscribed by the rotation of the crankpin 10, that is to say of the cylindrical casing inside which the crankpin turns.

Opposite the slot 7, the sheath 3 has a cutting 12 transverse to the axis 8. A finger 13 is engaged in this cutting 12 with a substantial axial play. The tool holder can thus move axially in the bore 2 between two limit stops formed by the walls 14 and 15 of the cutting 12. The position of the limit stop 14, that is to say its height measured along the axis 8 of the bore, on the one hand, and the relative position of the cutting 9, on the other hand, are such that when the tool holder is in abutment against the finger 13 via its limit stop 14, the width of the cutting 9, that is to say the length of the drive groove, extends over the whole axial travel of the crankpin 10 and even further. Consequently, in this axial position of the tool holder, the crankpin 10 does not come into contact with the walls of the cutting 9 and the tool holder is not driven in an axial movement, but only in an alternating rotation with an angular amplitude A1+A2.

In contrast, when the tool holder is in abutment via its limit stop 15, as represented in FIG. 2, the cutting 9 is offset relative to the axial travel of the crankpin 10, so that this crankpin abuts against the upper face 9a of the cutting 9, as represented by the position 10' in dot-and-dash lines, so that the tool holder is driven in an axial movement. The width of the cutting 12 must of course be at least equal to the amplitude of the alternating axial movement imposed by the crankpin 10. The tool holder occupies the position represented in FIG. 1 when the operator causes the tool 6 to penetrate into the canal of a tooth 16, by exerting a force F1, the effect of which is to generate a reaction R1 which pushes the tool holder back. Consequently, as long as the operator exerts a penetrative pressure, the tool is driven only in a rotational movement. The operator does not therefore feel any vibration due to a series of percussions.

In contrast, when the operator begins a movement for withdrawing the tool, that is to say a force F2, the friction of the tool 6 in the tooth generates a reaction R2 which pulls the tool holder in the direction of the tooth. The tool holder then occupies the position represented in FIG. 2, in which it is driven in a combined rotational and translational movement.

Figure 4:
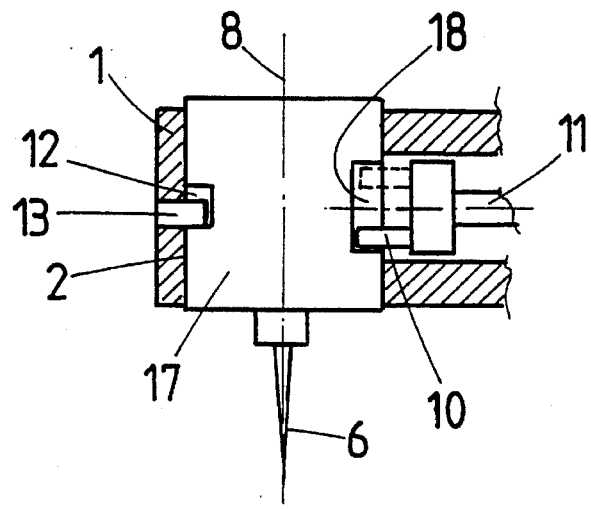
FIG. 4 represents, in a view similar to FIG. 1, a first alternative embodiment.
Figure 5:
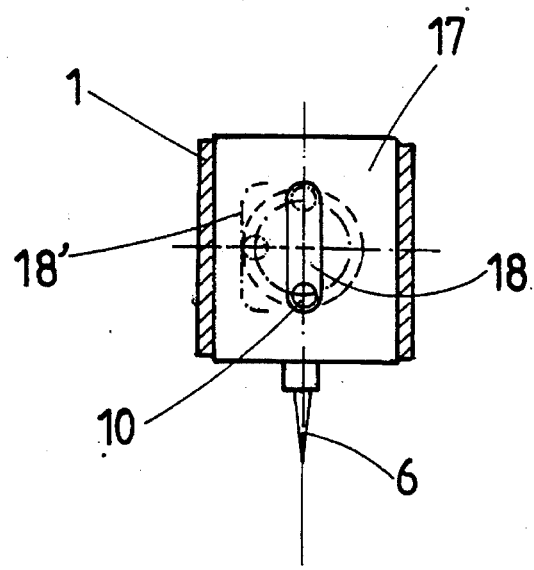
FIG. 5 is an elevation view of the embodiment represented in FIG. 4, viewed from the drive shaft.

In the embodiment described hereinabove, the tool holder consists of two components 3 and 4 for constructional reasons relating to the design of the system for clamping the mandrels belonging to the Applicant. In a general manner, particularly in a conventional design of the device for clamping the mandrel, with clip and spring, the tool holder can be made in only one piece, as represented in FIGS. 4 and 5, in which the tool holder 17 is represented by a cylinder in which can be seen the cutting 12 and an oblong groove 18 parallel to the axis 8, in which groove the crankpin 10 is engaged. The length of the groove 18 satisfies the conditions relating to the width of the cutting 9 in the first embodiment. In FIG. 5, dot-and-dash lines have been used to represent two other positions of the crankpin 10 and one of the end positions 18' of the groove 18 when the tool holder 17 is driven only in rotation, as is the case in the position represented in FIG. 4.

The axial play of the tool holder and its limit stops can be formed in a number of other ways. Exemplary embodiments are represented in FIGS. 6 to 9. In order to simplify matters, the tool holder has been designated by the reference 17 in the four alternatives.

Figure 6:
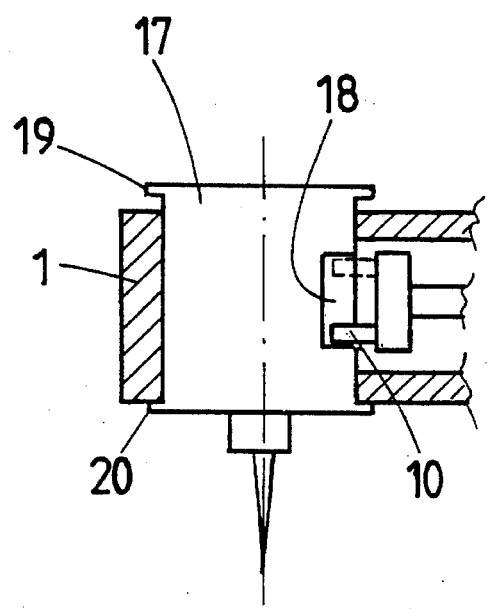
FIG. 6 represents diagrammatically a second alternative embodiment.

In the embodiment represented in FIG. 6, the limit stops consist of two flanges 19 and 20 formed at the ends of the tool holder 17. These flanges abut against the lower and upper faces of the head 1.

Figure 7:
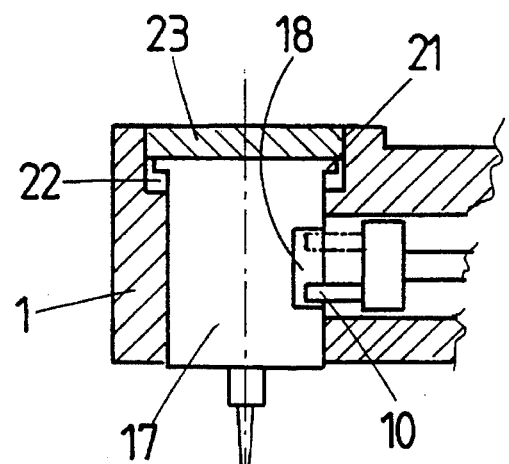
FIG. 7 represents diagrammatically a third alternative embodiment.

In the embodiment represented in FIG. 7, the tool holder 17 has a flange 21 at its upper end. This flange is displaced axially in a recess 22 of the head 1, between the base of this recess and a cap 23 constituting the other limit.

Figure 8:
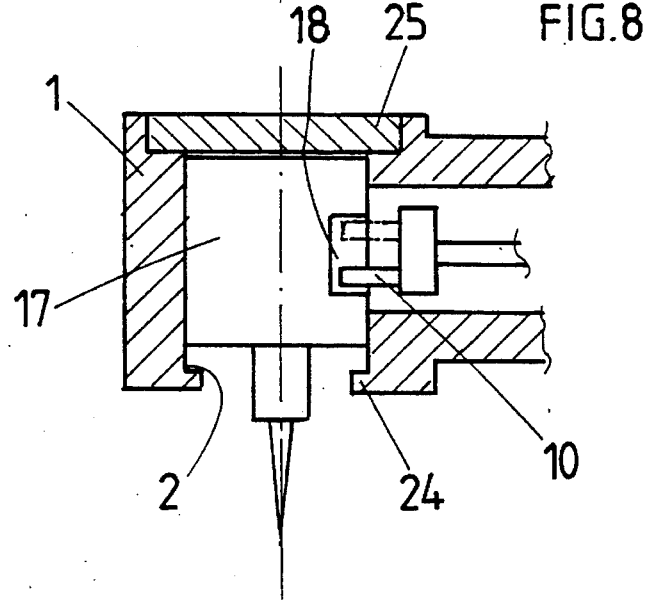
FIG. 8 represents diagrammatically a fourth alternative embodiment.

In the embodiment according to FIG. 8, the limit stops consist, on the one hand, of a rim 24 formed at the lower end of the bore 2 and, on the other hand, of a cap 25 closing the other end of the bore 2.

Figure 9:
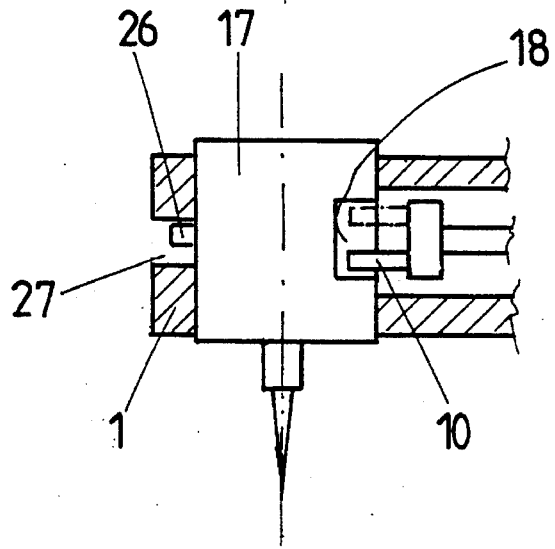
FIG. 9 represents diagrammatically a fifth alternative embodiment.

In the embodiment represented in FIG. 9, the tool holder 17 is equipped with a radial finger 26 engaged with play in a cutting 27 of the head 1.

I claim:

1. A contra-angle head for an endodontic instrument, comprising a bore (2) in which is mounted a cylindrical tool holder (3, 4; 17) having a groove extending (7, 9; 18) parallel to the axis of the bore and in which is engaged a crankpin (10) supported in an eccentric manner by a drive shaft (11) driven in a rotational movement in such a way as to drive the tool holder in its bore both in an alternating rotational movement and in an alternating translational movement, wherein the groove has a predetermined length and ends, the length of the groove (7, 9; 18) being greater than the outer diameter of the circle circumscribed by the crankpin (10), and further comprising axial play means for providing axial play of said holder in the head, said axial play means including two limit stops (14, 15; 19, 20; 24, 25; 21, 23) and cooperating surfaces for engaging the limit stops providing axial play for said holder in the bore, the position of these limit stops relative to the ends of the groove, viewed in a direction parallel to the axis of the bore, being such that when the tool holder is pushed back and the cooperating surfaces engage against one of the limit stops, the groove extends over at least the whole axial travel of the crankpin, such that the tool holder is not driven in translation during the rotation of the crankpin, and when the cooperating surfaces are in abutment against the other limit stop, the axial offset between the groove and the axial travel of the crankpin ensures that the tool holder is driven in translation.

2. The invention in accordance with claim 1 wherein the two limit stops are provided on the tool holder and the cooperating surfaces are on a finger on the head.

* * * * *